United States Patent [19]

Thelwall et al.

[11] 4,284,763

[45] Aug. 18, 1981

[54] SUGAR ACETALS, THEIR PREPARATION AND USE

[75] Inventors: Leslie A. W. Thelwall, Swindon; Leslie Hough, Wimbledon; Anthony C. Richardson, Henley-on-Thames, all of England

[73] Assignee: Talres Development (N.A.) N.V., Curacao, Netherlands Antilles

[21] Appl. No.: 133,975

[22] Filed: Mar. 26, 1980

[30] Foreign Application Priority Data

Apr. 6, 1979 [GB] United Kingdom ............... 12263/79

[51] Int. Cl.³ .......................... C07H 5/02; C07H 9/02
[52] U.S. Cl. ....................................... 536/4; 536/120; 536/122
[58] Field of Search ................................... 536/4, 120

[56] References Cited

U.S. PATENT DOCUMENTS

| | | |
|---|---|---|
| 3,598,804 | 8/1971 | Hindley et al. .......................... 536/4 |
| 3,723,412 | 3/1973 | Hicks et al. ............................. 536/4 |
| 3,751,409 | 8/1973 | Lee ........................................ 536/4 |

*Primary Examiner*—Johnnie R. Brown
*Attorney, Agent, or Firm*—Ostrolenk, Faber, Gerb & Soffen

[57] ABSTRACT

Novel sugar acetals such as those of formula

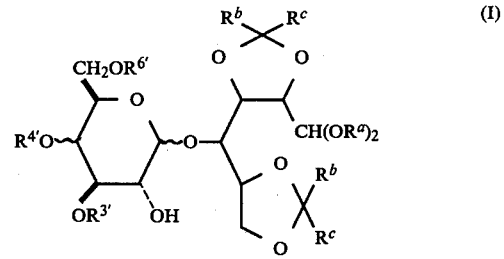

where $R^a$ is hydrocarbyl; $R^b$ and $R^c$ are hydrogen or hydrocarbyl; $R^{3'}R^{4'}$ and $R^{6'}$ are hydrogen or $R^{4'}$ with $R^{3'}$ or $R^{6'}$ is

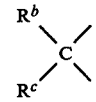

are made from 1,4-linked reducing disaccharides by a new exchange acetalation process in which the solvent is omitted. The sugar acetals have free hydroxy groups on the ring which groups can be converted to other substituents, e.g. chlorodeoxy or fatty acid acyl. After deprotection, the corresponding derivative of the initial disaccharide is obtained.

10 Claims, No Drawings

SUGAR ACETALS, THEIR PREPARATION AND USE

This invention relates to acetals of sugars.

Cyclic acetals of sugars and related compounds such as glycosides are well known as intermediates in the synthesis of derivatives of sucrose and other sugars. The preparation and use of sugars whose hydroxy functional groups are blocked by acetal groups is discussed for example by A. N. de Belder in Adv. Carbohydr. Chem. Biochem., 1977 34, 179–241.

Cyclic acetal groups are conventionally introduced on to saccharide and other carbohydrate molecules by reaction of the carbohydrate in the presence of a suitable acid catalyst with the appropriate aldehyde or ketone.

Recently, acetal exchange has been employed as an alternative mode of introduction. Such a reaction is considered to be under kinetic control, rather than under the thermodynamic control which prevails for the direct reaction of the carbohydrate with the aldehyde or ketone. As a consequence, the exchange reaction can lead to products which are not otherwise obtainable.

The reagent system used for the exchange reaction is typically 2,2-dimethoxypropane in N,N-dimethylformamide ('DMF') with a trace of p-toluenesulphonic acid ('ptsa'). With methyl α-D-glucopyranoside, for instance, this reagent system gives 4,6-O-isopropylidine-α-D-glucoside, whereas the direct reaction of acetone with methyl α-D-glucopyranoside gives at best a low yield of isopropylidine derivative (see M. E. Evans et al, Carbohydrate Res., 1967 3, 453–462, particularly at page 454).

We find however that the known reagent system for exchange acetalation does not work efficiently with 1,4-linked reducing disaccharide sugars such as lactose. Lactose when treated with 2,2-dimethoxypropane and ptsa in DMF gives a complex mixture which is difficult to characterise.

We have now found that the exchange reaction can be made to work for 1,4-linked reducing disaccharides by using a modification of the known reagent system in which the DMF or other conventional aprotic polar solvent is omitted. Such a reaction produces novel acetals which as with the known acetals of other sugars are useful synthetic intermediates.

Thus, in one aspect, the present invention provides a process for preparing novel acetals of 1,4-linked reducing disaccharide sugars which process comprises reaction of such a sugar with an exchange acetalation reagent in the presence of an acid catalyst but in the absence of added solvent.

The reaction conditions employed for the present process are not critical, nor is the nature of the exchange acetalation reagent. This said, it is preferred that the exchange acetalation reagent is liquid at the temperature of the reaction. The 1,4-linked reducing disaccharide sugars are relatively stable, compared for example with sucrose, which in turn makes it possible to effect the present process at between 50° and 150° C. Lower temperatures can be used, though at below 25° C. the reaction is often too slow to be of much interest. Higher temperatures can also be used, though the temperature should not be above the boiling point of the exchange acetalation reagent.

More generally, it is preferred to effect the present reaction with reflux of the reaction mixture.

Conveniently the exchange acetalation reagent is of the formula $R^bC(OR^a)_2R^c$, where $R^a$ is a hydrocarbyl group, $R^b$ is hydrogen or a hydrocarbyl group, and $R^c$ is hydrogen or a hydrocarbyl group. Suitable hydrocarbyl groups for $R^a$, $R^b$ and $R^c$ include alkyl, aryl and aralkyl groups, with $C_1$ to $C_3$ alkyl, phenyl and benzyl groups being particularly suitable. The groups $R^a$, $R^b$ and $R^c$ form part of the protecting acetal groups in the sugar acetals prepared by the process, and since in most instances these protecting groups are eventually removed, it will be apparent that their nature is not of great importance.

Particularly preferred exchange acetalation reagents are those in which both groups $R^a$ are the same group: these reagents can readily be made from the corresponding ketone $R^b COR^c$ by reaction of the ketone with the alcohol $R^aOH$. In order to avoid production of isomer mixtures, it is also preferred that the groups $R^b$ and $R^c$ are the same.

2,2-dimethoxypropane is the exchange acetalation reagent which we currently use. It boils at around 83° C. and is simply prepared from acetone and methanol.

As in the conventional exchange acetalation reactions, the present process employs an acid catalyst. Any of the known catalysts can be used, with ptsa being particularly suitable.

The exchange acetalation reagent is preferably employed in molar excess relative to the disaccharide. Suitably from 1 to 30 g of reagent is used for every 1 g of disaccharide, with the weight ratio preferably being from 3:1 to 10:1, more preferably around 4:1 to 8:1.

With a reaction embodying the invention, it is usually found that the reducing sugar of the disaccharide (ie. the aglycone sugar linked by its oxygen at carbon (4) to the carbon (1) of the other, glycoside sugar) is reactive and undergoes ring opening, while the non-reducing sugar is less reactive and does not ring-open.

Thus, the novel acetal products obtained by the present process typically have a peracetalated chain derived from the reducing sugar. Such a preacetalated chain will be linked by its oxygen at carbon (4) to the carbon (1) of the ring of the non-reducing sugar and bear a cyclic acetal at carbons (2) and (3) and carbons (5) and (6), together with a simple acetal at carbon (1).

The ring of the non-reducing sugar is at most partially acetalated in the reaction. If reaction on the non-reducing sugar does occur then a cyclic acetal is formed, the ring maintaining its integrity.

Thus, in a second aspect, the present invention provides novel sugar acetals of the general formula

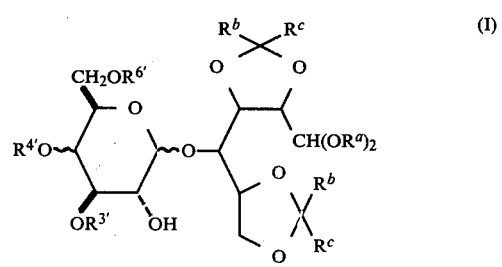

(I)

wherein:
the two groups $R^a$ are the same and are hydrocarbyl groups, preferably alkyl, aryl or aralkyl groups and more preferably $C_1$ to $C_3$ alkyl, phenyl or benzyl groups;

$R^b$ is hydrogen or a hydrocarbyl group preferably as preferred for $R^a$;

$R^c$ is hydrogen or a hydrocarbyl group preferably as preferred for $R^a$, and is preferably the same as $R^b$;

$R^{3'}$, $R^{4'}$ and $R^{6'}$ are hydrogen atoms or $R^{3'}$ and $R^{4'}$, or $R^{4'}$ and $R^{6'}$ together form a group of formula

in which $R^b$ and $R^c$ are as defined, the remaining group $R^{3'}$ or $R^{6'}$ being a hydrogen atom.

Examples of 1,4-linked reducing disaccharides which can in practice be employed in the present invention include lactose, maltose and cellobiose.

With lactose, whose formula is

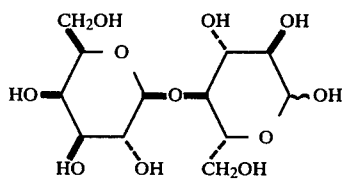 (II)

the predominant product of the invention formed with for instance an exchange acetalation reagent which is a symmetrical gem-dialkoxyalkane of formula $R^1 C(OR^d)_2 R^1$, where $R^1$ and $R^d$ are $C_1$ to $C_3$ alkyl groups, is a novel tetraacetal of the invention:

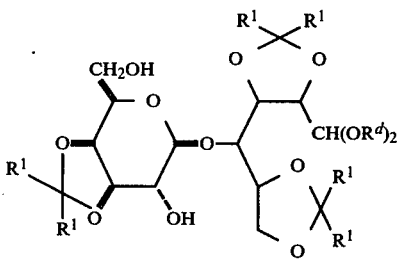 (III)

It is significant to note that such a compound (III) cannot be detected in the complex mixture obtained when lactose is reacted with the conventional reagent system for the exchange reaction.

For maltose, whose formula is

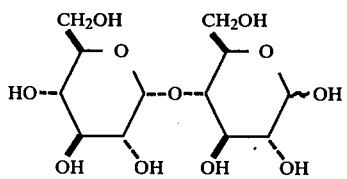 (IV)

the predominant product of the corresponding reaction is an approximately equimolar mixture of two novel compounds of the invention:

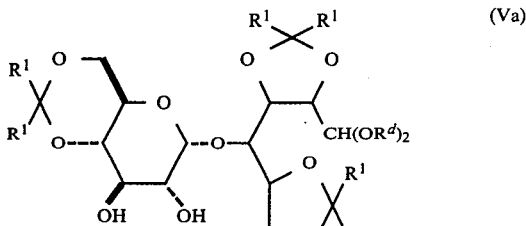 (Va)

and

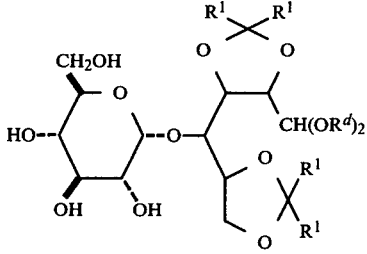 (Vb)

while for cellobiose

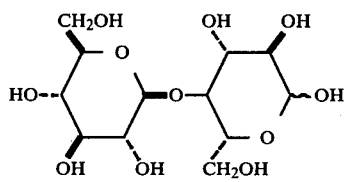 (VI)

the product corresponding to products (III) and (Va) is the novel compound

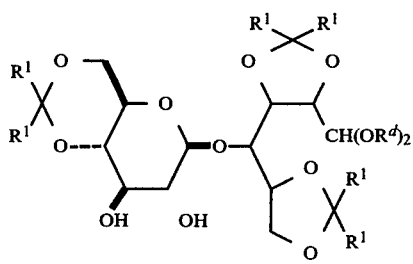 (VII)

These and other sugar acetals in accordance with the invention and of formula (I) have two or four free hydroxy groups on the non-reducing ring, with the remaining hydroxy groups of the disaccharide being protected. The free hydroxy groups are at C-2' and one of C-3', C-4' and C-6' if there are two such groups, or at C-2', C-3', C-4' and C-6' if there are four such groups.

One or more of the free hydroxy groups can easily be converted to other substituents and thus lead to useful sugar derivatives. Free primary hydroxy groups as at C-6' are more reactive than free secondary hydroxy groups as at C-2', C-3' and C-4', and this difference in reactivity can be used to advantage, either to introduce a desired substituent at a primary position or to introduce a desired substituent at a secondary position after first selectively introducing a protecting group at a primary position.

After introduction of the desired substituent or substituents, the acetal and any other protecting groups can be removed. Such deprotection is normally accompanied by ring closure of the ring of the reducing sugar, thereby giving a desired derivative of the reducing sugar.

By a process also in accordance with the present invention, a product with a free hydroxy group at carbon (6) of the glycoside ring (ie. at C-6') can be converted to its 6-chlorodeoxy derivative. Such a 6-chlorodeoxy derivative can be obtained for instance from a galactopyranoside and gives, after de-acetalation of the blocked hydroxy groups and accompanying reclosure of the ring of the reducing sugar, the 6-chlorodeoxy derivative of the original disaccharide. 6-Chlorodeoxy disaccharides are compounds in accordance with our UK Patent Application No. 10694/77 (published as its German equivalent, Offenlegungsschrift No. 2,811,040) which is concerned with anti-fertility agents. Chlorination may be effected directly eg. by reaction with sulphuryl chloride or indirectly eg. by introduction of a tosyl substituent at the carbon (6) and subsequent displacement with chloride ion.

As another example of the use of the present products as synthetic intermediates, and in a further process in accordance with the invention, one or more of the free hydroxy groups can be acylated with an acyl group derived from a fatty acid, thus giving after deblocking a fatty acid ester derived from the initial disaccharide. Acylation can optionally be preceded by protection of any free primary hydroxy groups, thereby giving acylation only at the free secondary positions. The resulting sugar esters, especially those of fatty acids having 12 to 22 carbons, include various compounds known to be useful as surface active agents.

The present invention is illustrated by way of the following Examples. In Example 1, certain compounds are identified as compounds of the formula:

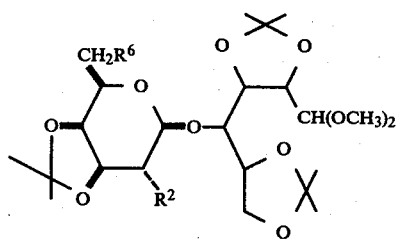

(VIII)

This and other compounds are named as 1,1-di-O methyl derivatives but can also be named as aldehyde dimethyl acetals. Similarly, in Example 2 certain compounds are identified as compounds of the formula:

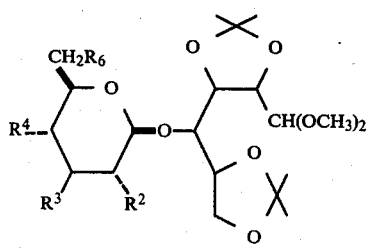

(IX)

EXAMPLE 1

(i)

4-O-(3,4-O-isopropylidene-$\beta$-D-galactopyranosyl)-2,3:5,6-di-O-isopropylidene-1,1-di-O-methyl D-glucose (VIIIa; $R^2=R^6=OH$)

A suspension of $\alpha$-lactose monohydrate (34.2 g) and p-toluenesulphonic acid (250 mg) in 2,2-dimethoxypropane (250 ml) was heated at reflux for about 2 hours. A clear solution was obtained and cooled to room temperature. After neutralization by stirring with Amberlite resin IR-45(OH$^-$), the resin was filtered off and the filtrate evaporated to a syrup, which was chromatographed on a column of silica gel. Elution with ethyl acetate-petrol (1:1 by volume) gave the tetra-acetal derivative VIIIa (24 g, 50%) which crystallized from methanol. Recrystallization from methanol afforded the compound as prisms, m.p. 133°–134°.

$[\alpha]_D^{23} = +39.1°$ (c, 1.0 CHCl$_3$), analysis for $C_{23}H_{40}O_{12}$: Found: C, 54.3%; H, 8.2% Calc: C, 54.3%; H, 7.9%

For confirmation of the structure, two derivatives were prepared by reaction at the unblocked hydroxy groups.

(ii)

4-O-(3,4-O-isopropylidene-2,5-di-O-mesyl-$\beta$-D-galactopyranosyl)-2,3:5,6-di-O-isopropylidene-1,1-di-O-methyl-D-glucose (VIIIb; $R^2=R^6=OSO_2CH_3$)

To a cooled solution (0° C.) of the compound (VIIIa) (0.5 g) in pyridine (10 ml) was added methanesulphonyl ("mesyl") chloride (0.2 ml) by dropwise addition. After complete addition, the reaction was stirred at room temperature until tlc (ethyl acetate-petrol, 5:1 by volume) indicated complete reaction. The mixture was then poured into ice-water and extracted several times with dichloromethane. The combined extracts were washed successively with 2 N-hydrochloric acid, saturated sodium bicarbonate solution and water, and then dried over anhydrous sodium sulphate. Removal of sodium sulphate by filtration and evaporation of the filtrate gave the dimesylate VIIb (0.4 g, 61%) as a syrup which crystallised from methanol, m.p. 142°–144°.

$[\alpha]_D^{23} = +10.9°$ (c, 1.0 CHCl$_3$), analysis for $C_{25}H_{44}S_2O_{16}$: Found: C, 45.1%; H, 6.6%. Calc: C, 45.2%; H, 6.6%

(iii)

4-O-(2,6-di-O-acetyl-3,4-O-isopropylidene-$\beta$-D-galactopyranosyl)-2,3:5,6-di-O-isopropylidene-1,1-di-O-methyl D-glucose (VIIIc; $R^2=R^6=OCOCH_3$)

10 g of compound VIIIa was dissolved in dry pyridine (100 ml) and cooled in an ice-bath. Acetic anhydride (10 ml) was added and the mixture was stirred at room temperature until tlc (ethyl acetate-petrol, 1:1 by volume) showed complete reaction. The reaction mixture was then poured into ice-water and extracted several times with dichloromethane. The combined extracts were processed in the same manner as for the dimesylate VIIIb to give the di-acetate VIIIc as a syrup which crystallised from methanol. Subsequent recrystallisation from ethanol (96%) afforded 11 g, 94% of the compound m.p. 113°–115°.

$[\alpha]_D^{23} = +25.2$ (c, 1.0 CHCl$_3$).

The compound (VIIIa) was then subjected to further reaction in order to provide new sugar derivatives.

(iv) Conversion to 6'-chlorodeoxy lactose

Compound (VIIIa) was treated in a conventional manner with the known chlorinating agent sulphuryl chloride. In this way, a chlorodeoxy group was introduced at the 6' position of the galactopyranosyl ring; there was little evidence of reaction at the 2' position but the 2'-hydroxy group would be expected to be considerably less reactive than the 6'-hydroxy group. The product was a compound (VIIId), where $R^2=OH$, $R^6=Cl$, as shown in particular by $^{13}C$ nmr studies where the peak assigned to C-6' in the parent compound (VIIIa) shifted by 20.2 ppm in the product compound, the shift being upfield. In addition after acetylation at C-2', the product ($R^2=OCOCH_3$, $R^6=Cl$) gave peaks in the mass spectrum (ms) at 555,553 and 265,263 indicating monochlorination.

Removal of the acetal groups from the compound (VIIId) in the usual way then gave the 6-chlorodeoxy lactose.

6'-chlorodeoxy lactose was also made by an alternative chlorination procedure.

The tetra-acetal (VIIIa, 2.03 g, 4 mmol) was dissolved in pyridine (50 ml) and cooled to 0° C. Triphenylphosphine (2.09 g, 8 mmol) was added followed by the addition of carbon tetrachloride (0.39 ml 4 mmol) in portions. The reaction was stirred at 0° C. for 10 minutes and then at 70°-80° C. for 1 hour, cooled and methanol (10 ml) added to decompose any excess reagent. The mixture was concentrated by co-distillation with toluene and then methanol, and fractionated on a dry-packed column of silica gel with 1:1 ethyl acetate-petrol as eluent. The 6'-monochloro derivative (VIIId, 1.42 g) was obtained as a syrup which crystallised on standing mp.=103° to 105° C. $[\alpha]_D^{21}=+38.2$ (c: 1.0, $CHCl_3$). Again, removal of the acetal groups gave 6'-chlorodeoxy lactose.

(vii) Conversion to lactose 2'-palmitate

Compound (VIIIa) was tritylated at the 6'-position, a palmitoyl group introduced at the 2'-position to give a compound (VIII g) where $R^2=OPm$, $R^6=Otrityl$, and the trityl and acetal groups removed to give the desired compound.

20 g of compound (VIIIa) was dissolved in 200 ml pyridine and reacted at 50° C. for 5 days with 16.5 g of trityl chloride. The 6'-Otrityl compound ($R^2=OH$, $R^6=Otrityl$) was purified by silica gel chromatography to give 16.2 g product, mp 123°-125° C., $[\alpha]_D^{21}=+18.9°$ (c: 1.0, $CHCl_3$).

A solution of the 6'-Otrityl compound (3 g) in pyridine (50 ml) was cooled to 0° C., and then treated with palmitoyl chloride (1.3 g) by dropwise addition. The mixture was stirred at room temperature for 2 days, and concentrated by co-distillation with toluene and then methanol. The residue was fractionated on a dry-packed column of silica gel, using 1:4 ethyl acetate-petrol as eluent. The 2'-palmitate, 6'-Otrityl compound (2.9 g) was obtained as a syrup which crystallised from ether-petrol, mp. 63°-64°.

Deprotection in conventional manner gave a white powder, lactose 2'-palmitate.

(v) Conversion to lactose 6'-palmitate

Compound (VIIIa) was reacted with palmitoyl chloride under standard conditions to give a palmitoyl ("Pm") group at the free 6' position, the product being compound VIIIe where $R^2=OH$, $R^6=OPm$.

A solution of the compound (VIIIa 1 g) in pyridine (20 ml) was cooled to 0° C. and then treated with palmitoyl chloride (0.7 ml) The reaction was stirred at room temperature for 24 hours, the mixture poured into ice-water and then extracted with dichloromethane. The organic phase was washed successively with 2 N-HCC, saturated sodium carbonate solution and water, and then dried over anhydrous sodium sulphate. Evaporation of the solvent produced a syrup, which was fractionated by dry-packed column chromatography on silica gel, using 1.2 ethyl acetate-petrol as eluent. The 6'-palmitate (VIIIe) was obtained as a white powder (950 mg).

Evidence for this product included a mass spectrum which was consistent only with introduction of one palmitoyl group per molecule of compound VIIIa, the ms showing a peak of 441 of 1.1% intensity of the base peak.

Removal of the acetal groups in the usual way then gave lactose 6'-palmitate.

(vi) Conversion to lactose 2',6'-dipalmitate

Compound (VIIIa) was reacted with excess palmitoyl chloride to give palmitoyl groups at the free 2' and 6' positions, the product being the compound (VIIIf) where $R^2=R^6=OPm$.

The compound (VIIIa, 3 g) was dissolved in pyridine (50 ml) and cooled to 0° C. Palmitoyl chloride (3.6 g) was added dropwise to the mixture, which was then stirred at room temperature for about 24 hours. The reaction mixture was concentrated by co-distillation with toluene and then methanol, and fractionated on a dry-packed column of silica gel, using 1:4 ethyl acetate-petrol as eluent. The di-palmitate (VIIIf) was isolated as a waxy solid (2.6 g). which gave a ms peak at 679, intensity 1.7% corresponding to a doubly charged ion with the mass of the desired compound.

Deprotection then gave the desired compound, lactose 2',6'-di-palmitate.

EXAMPLE 2

(i)

4-O-(4,6-O-isopropylidene-α-D-glucopyranosyl)-2,3:5,6-di-O-isopropylidene-1,1-di-O-methyl D-glucose (IXa; $R^2=R^3=OH$, $R^4$ with $R^6=-OC(CH_3)_2O-$) and 4-O-(α-D-glucopyranosyl)-2,3:5,6-di-O-isopropylidene-1,1-di-O-methyl D-glucose (IXb; $R^2=R^3=R^4=R^6=OH$)

To a suspension of maltose (50 g) in 2,2-dimethoxypropane (200 ml) was added p-toluenesulphonic acid (0.1 g) and the mixture heated under reflux for 8 hours. The resultant solution was then cooled, neutralized with Amberlite resin IR-45(OH−) and concentrated to a brown syrup. Tlc (chloroform-methanol, 10:1 by volume) indicated that it contained two major components and several minor products. Chromatographic fractionation of the mixture on silica gel (500 g) with chloroform-methanol (50:1 by volume) as eluent gave the two major components in pure form.

The more mobile component (16 g, 22%) was isolated in crystalline form and found to be 4-O-(4,6-O-isopropylidene-α-D-glucopyranosyl)-2,3:5,6-di-O-isopropylidene-1,1-di-O-methyl D-glucose, (IXa), ie. a compound wherein the aglycone glucose had reacted to give a peracetalated chain and one cyclic acetal was introduced on the glucopyranoside moeity. Recrystallization from toluene-cyclohexane gave crystals, mp. 132–133.

The less mobile component (12 g, 18%) was isolated as a foam and shown to be 4-O-α-D-glucopyranosyl-2,3:5,6-di-O-isopropylidene-1,1-di-O-methyl D-glucose, (IXb) ie. a compound wherein the aglycone glucose had reacted to give a peracetalated chain but wherein the glucopyranoside moiety was unchanged.

$[\alpha]_D^{23} = +191.7$ (c, 1.0 CHCl$_3$)

For confirmation of the respective structures IXa and IXb, various derivatives were prepared by reaction at the unblocked hydroxy groups.

(ii)
4-O-(2,3-di-O-acetyl-4,6-O-isopropylidene-α-D-glucopyranosyl)-2,3:5,6-di-O-isopropylidene-1,1-di-O-methyl D-glucose (IXc; $R^2=R^3=OCOCH_3$, $R^4$ with $R^6 = -OC(CH_3)_2O-$).

Acetylation was accomplished in a manner similar to the procedure used in Example 1 (iii) and employing acetic anhydride in pyridine. The resultant di-O-acetate IXc was a syrup.

$[\alpha]_D^{23} = +66$ (c, 1.0 CHCl$_3$): Analysis for $C_{27}H_{44}O_{14}$: Found: C, 55.1%, H, 7.9% Calc. C, 54.7% H, 7.5%

(iii)
4-O-(2,3,4,6-tetra-O-acetyl-α-D-glucopyranosyl)-2,3:5,6-di-O-isopropylidene-1,1-di-O-methyl-D-glucose (IXd; $R^2=R^3=R^4=R^6=OCOCH_3$)

Acetylation in the same way as for the preceding compound gave the tetra-O-acetate IXd in crystalline form. Recrystallization from ether-light petroleum gave crystals mp. 109°–110° C.

$[\alpha]_D^{23} = +85$ (c, 1.0 CHCl$_3$): Analysis for $C_{28}H_{44}O_{16}$: Found: C, 52.8%; H, 7.2% Calc: C, 52.8%; H, 6.95%

The compound IXa, the tetra-acetyl, was then subjected to further reaction in order to lead to new sugar derivatives.

(iii) Conversion to the corresponding 2,3-ditosyl compound

Tosyl (ie. toluenesulphonyl) chloride (1.58 g, 2.2 moles) was added to a cooled solution of the tetra-acetal (IXa) (1 g) in dry pyridine (15 ml). The reaction mixture was left at room temperature for 24 hours and then kept at 60° for 4 hours. Isolation was accomplished in the usual way by pouring the reaction mixture in to water and extraction of the product with chloroform. The ditosylate IXe; $R^2=R^3=OSO_2C_6H_4CH_3$, $R^4$ with $R^6 = -OC(CH_3)_2O-$; was crystallized from aqueous alcohol to give 0.85 g (55%) of crystals, mp. 69°–70°.

$[\alpha]_D^{23} = +48$ (c 1.0 CHCl$_3$)

(iv) Conversion to the corresponding 2-tosyl compound

A solution of tosyl chloride (0.79 g 1.1 moles) in dry pyridine (15 ml) was added dropwise to a cooled solution of compound IXa (1 g) in dry pyridine (15 ml) over approximately 30 minutes and the reaction mixture then left at room temperature for 8 hours. The mono (2) tosylate IXf; $R^2=OSO_2C_6H_4CH_3$, $R^3=OH$, $R^4$ with $R^6 = -OC(CH_3)_2O-$; was then isolated as above (0.68 g, 53%) to give crystals mp. 68°–69° (ethanol-water).

$[\alpha]_D^{23} = +66.5$ (c, 1 CHCl$_3$)

(v) Conversion to the corresponding 2,3-dimesyl compound

Conventional mesylation of Compound IXa using mesyl chloride in pyridine gave a crystalline di-O-mesylate IXg; $R^2=R^3=OSO_2CH_3$, $R^4$ with $R^6=-OC(CH_3)_2O-$; in 63% yield mp. 70°–71° (ethanol-water).

$[\alpha]_D^{23} = +55$ (c, 1.0 CHCl$_3$).

We claim:

1. A sugar acetal of the general formula

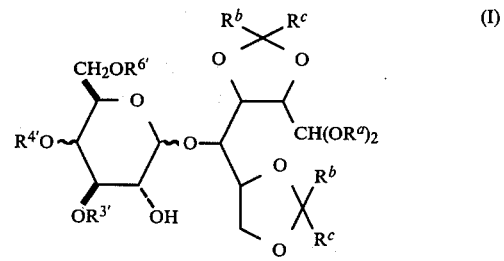

(I)

wherein:

$R^a$ is $C_{1-3}$ alkyl, phenyl or benzyl;

$R^b$ is hydrogen, $C_{1-3}$ alkyl, phenyl or benzyl;

$R^c$ is hydrogen, $C_{1-3}$ alkyl, phenyl or benzyl;

$R^{3'}$, $R^{4'}$ and $R^{6'}$ are hydrogen atoms or one of $R^{3'}$ and $R^{6'}$ is a hydrogen atom and the other or $R^{3'}$ and $R^{6'}$ forms with $R^{4'}$ a group of formula

in which $R^b$ and $R^c$ are as defined.

2. The sugar acetal of claim 1 wherein said group $R^b$ is the same as said group $R^c$.

3. A sugar acetal of the formula

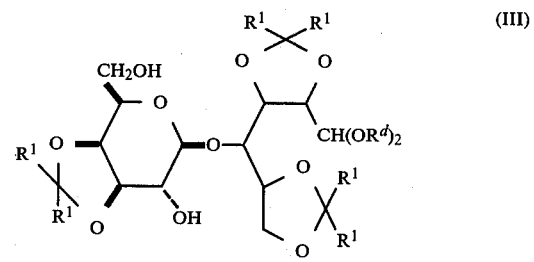

(III)

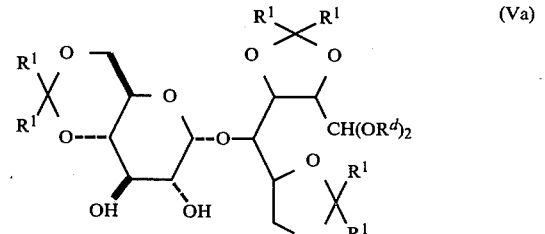

(Va)

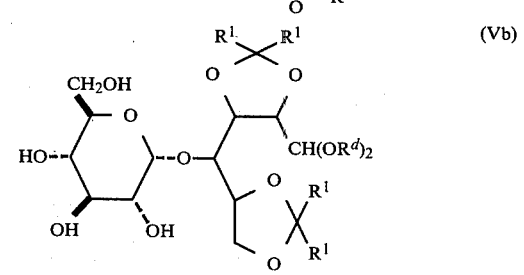

(Vb)

-continued

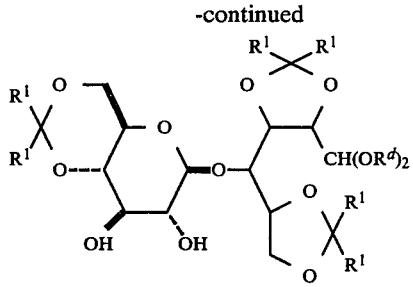
(VII)

wherein $R^1$ is a $C_1$ to $C_3$ alkyl group, and $R^d$ is a $C_1$ to $C_3$ alkyl group.

4. 4-O-(3,4,-O-isopropylidene-β-D-galactopyranosyl)-2,3:5,6-di-O-isopropylidene-1,1-di-O-methyl D-glucose.

5. 4-O-(4,6-O-isopropylidene-α-D-glucopyranosyl)-2,3:5,6-di-O-isopropylidene-1,1-di-O-methyl D-glucose.

6. 4-O-(α-D-glucopyranosyl)-2,3:5,6-di-O-isopropylidene-1,1-di-O-isopropylidene-1,1-di-O-methyl D-glucose.

7. In a process for preparing a sugar acetal in which 1,4-linked reducing disaccharide sugar is reacted with an exchange acetalation reagent in the presence of an acid catalyst, the improvement which comprises effecting the reaction in the absence of added solvent and recovering the sugar acetal of claim 1 formed thereby.

8. The process of claim 7 wherein said reaction is effected with reflux.

9. The process of claim 7 wherein said exchange acetalation reagent is 2,2-dimethoxypropane.

10. The process of claim 7 wherein said sugar is lactose, maltose or cellobiose.

* * * * *